(12) United States Patent
Wilmes

(10) Patent No.: US 9,091,672 B2
(45) Date of Patent: Jul. 28, 2015

(54) RETAINING DEVICE FOR A PIPETTING NEEDLE

(71) Applicant: Siemens Healthcare Diagnostics Products GmbH, Marburg (DE)

(72) Inventor: Hugo Wilmes, Bad Soden (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 0 days.

(21) Appl. No.: 14/206,603

(22) Filed: Mar. 12, 2014

(65) Prior Publication Data

US 2014/0271405 A1   Sep. 18, 2014

(30) Foreign Application Priority Data

Mar. 13, 2013 (EP) .................................... 13158896

(51) Int. Cl.
*G01N 35/10* (2006.01)
*B01L 3/00* (2006.01)

(52) U.S. Cl.
CPC ......... *G01N 35/1079* (2013.01); *B01L 3/50825* (2013.01)

(58) Field of Classification Search
CPC . G01N 35/1079; G01N 35/10; B01L 3/50825
See application file for complete search history.

(56) References Cited

U.S. PATENT DOCUMENTS

| 2004/0054286 | A1 | 3/2004 | Audain et al. |
| 2007/0053797 | A1 | 3/2007 | Muraishi et al. |
| 2007/0095159 | A1 | 5/2007 | Champseix et al. |
| 2008/0292501 | A1* | 11/2008 | Sattler et al. ................. 422/68.1 |
| 2010/0111769 | A1* | 5/2010 | Ding .............................. 422/100 |
| 2012/0100047 | A1 | 4/2012 | Brutler et al. |

FOREIGN PATENT DOCUMENTS

WO      2010082080 A1    7/2010

OTHER PUBLICATIONS

European Search Report and Written Opinion of European patent Application No. 13158896.4 dated Sep. 13, 2013 (8 Pages).

* cited by examiner

*Primary Examiner* — Jill Warden
*Assistant Examiner* — Matthew Krcha
(74) *Attorney, Agent, or Firm* — Dugan & Dugan, PC

(57) ABSTRACT

The invention relates to a retaining device (1) for a hollow needle (12) of a pipetting device in an automatic analysis apparatus. The retaining device (1) comprises a first retaining element (2), which can be secured releasably on a base plate that is movable in an automated manner, and a second retaining element (4), which is connected to the first retaining element (2), wherein at least one bearing bushing (14) is provided, which is fixed between the retaining elements (2, 4) and in which the hollow needle (12) is mounted.

10 Claims, 4 Drawing Sheets

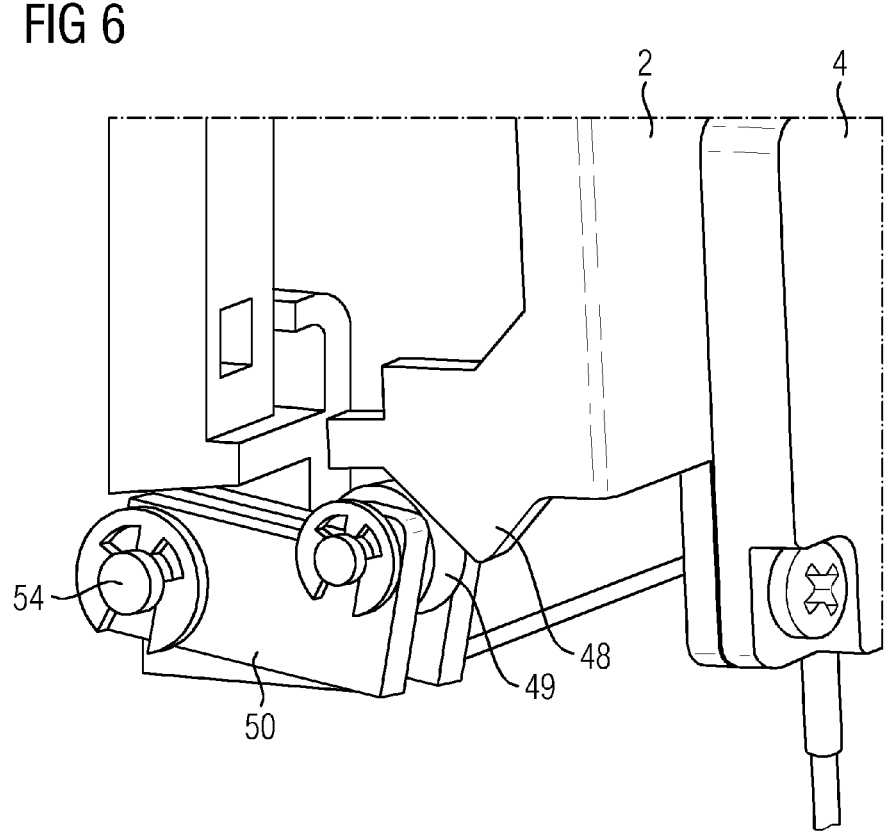

RETAINING DEVICE FOR A PIPETTING NEEDLE

Figure 1:
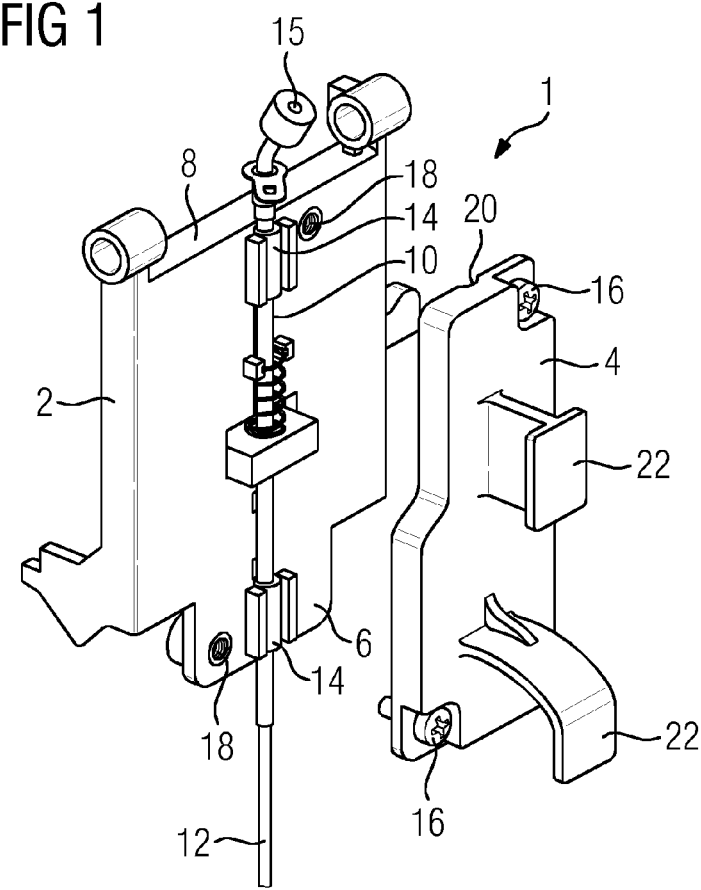

The invention relates to a retaining device for a hollow needle for puncturing the lid of a sample tube in an automatic analysis apparatus.

Numerous detection and analysis methods for determining physiological parameters in samples of bodily fluid or in other biological samples are nowadays carried out in large numbers in an automated manner in automatic analysis apparatus, also called in vitro diagnostic systems.

In order to be able to carry out a multiplicity of tests in an automated manner, various devices for the spatial transfer of sample containers, reaction containers and reagent containers are needed, e.g. transfer arms with gripping function, conveyor belts or rotatable conveyor wheels. Moreover, pipetting devices are provided for the transfer of liquids. The analysis apparatus also comprise a control unit which, by means of suitable software, is able to plan and execute the work steps for the desired analyses in a substantially independent manner.

Many of the measurement systems used in automated analysis apparatus of this kind are based on optical methods. These methods permit the qualitative and quantitative detection of analytes in liquid samples. Clinically relevant parameters, such as the concentration or the activity of an analyte, are often determined by means of a portion of a bodily fluid of a patient, e.g. blood, plasma, serum or urine, being mixed with one or more test reagents in a reaction vessel, as a result of which a biochemical reaction is started which brings about a measurable change in an optical or other physical property of the test mixture.

The samples are usually delivered to the apparatus in sample vessels, e.g. blood sampling tubes. Blood sampling tubes are usually made of transparent plastic and are equipped at the tip with a special connector for cannulas. Except in the case of the so-called Sarstedt principle, blood sampling tubes are often designed as negative-pressure systems, i.e. a negative pressure prevails within the sample vessel from the outset. When it is plugged onto the adapter connected to the puncturing cannula, blood is suctioned as a result of this negative pressure. An advantage of this system is that the amount of blood suctioned is comparatively constant, and it is thus also possible to precisely measure the amount of an anticoagulant (e.g. citrate, EDTA, heparin) introduced beforehand into the blood sampling tube. The blood sampling tubes are usually sealed by an elastic seal in order to maintain the pressure.

To be able to carry out a test in an automated manner, it is necessary to remove an aliquot of the blood sample from the blood sampling tube and transfer it into the reaction vessel intended for the particular test. For this purpose, pipetting devices are provided in the analysis apparatus. Conventional pipetting devices comprise a hollow needle, which is secured by means of a retaining device and which, operated by pressure or negative pressure, can remove and discharge defined amounts of samples. Needles of this kind have a substantially cylindrical basic shape with a central hollow channel, wherein the hollow needle can have axial portions with varying internal and external radii. A circle is usually chosen as the basic surface area of the cylinder, although other basic shapes are possible. The tip of the needle is usually shaped conically or, if it is intended to puncture the lid of closed blood sampling tubes or other liquid receptacles, sharpened with a beveled edge.

To remove sample liquid from a sample container, the hollow needle is guided along the center axis of the sample tube, punctures the elastic sealing stopper and is thus immersed into the sample liquid. The immersion is usually registered by means of a corresponding sensor, and the predefined amount is suctioned with compressed-air control.

Since the hollow needle has a comparatively robust design and the elastic stoppers of sample tubes are made from solid rubber with a thickness of up to 1 cm, a relatively high force is needed to puncture a sealing stopper. Here, a displacement of the needle can lead to errors in the sampling procedure and to corresponding subsequent errors in the evaluation of the sample. Furthermore, the needle becomes worn over the course of a large number of puncturing procedures, and therefore the hollow needle has to be regularly replaced.

The object of the invention is therefore to make available a retaining device for a hollow needle for puncturing the lid of a sample tube, which retaining device affords a particularly stable hold of the hollow needle and at the same time permits simple replacement of the hollow needle in the event of wear.

According to the invention, this object is achieved by the fact that the retaining device comprises a first retaining element, which can be secured releasably on a base plate that is movable in an automated manner, and a second retaining element, which is connected releasably to the first retaining element, wherein at least one bearing bushing is provided, which is fixed between the retaining elements and in which the hollow needle is mounted.

This results in a good bearing and thus a stable hold and a precise positioning of the hollow needle in the radial direction, which is necessary for the puncturing accuracy of the hollow needle. A further advantage lies in the easy replaceability of the hollow needle and in the fact that, after replacement, the needle does not have to be adjusted again. Here, a releasable connection of the retaining device on a base plate of the automatic analysis apparatus, which base plate is movable in an automated manner, ensures stable positioning, such that the new hollow needle is also precisely positioned like the previous hollow needle. By releasing the connection, a worn hollow needle can be removed together with the retaining device, and a new hollow needle with retaining device can be fitted. A connection of the new retaining device fixes the new hollow needle in the at least one bearing bushing.

In an advantageous embodiment, the first retaining element comprises a hollow space in which an abutment secured on the hollow needle is enclosed, in such a way that the movement of the hollow needle in the bearing bushing is limited. The bearing bushing in fact has the further advantage that an axial movement of the hollow needle is possible. This permits detection of unintended contact of the needle, a so-called crash, e.g. with the inside wall of the blood sampling tube. In the event of a crash, the needle in the hollow space deflects axially, which can be detected by corresponding detectors. However, this deflection movement should be limited, since otherwise the positioning and stability of the hollow needle are compromised. Moreover, in the event of desired contact, i.e. upon puncturing of the seal of the blood sampling tube, a sufficient force has to be able to be exerted in the axial direction. For this purpose, the hollow needle has an abutment, which advantageously extends in the radial direction. The first retaining element has a hollow space that encloses the abutment but does not fix it, instead permitting an axial movement that is limited only in respect of its width.

Advantageously, a restoring element is assigned to the hollow needle. It is thereby ensured that, despite the mobility of the hollow needle in the axial direction, a predefined standard position exists to which the hollow needle spontaneously returns without being acted on by an external force, e.g. after a deflection movement of the hollow needle as a result of a crash. The predefined standard position also makes it easier to detect such a crash by means of a corresponding crash sensor.

The restoring element is advantageously a spring secured between abutment and first retaining element. In the state free of force, i.e. without contact between the needle and a resistance, a standard position is thus defined in what is a particularly simple manner from the technical point of view.

In another advantageous embodiment, the abutment comprises a bolt, which is connected to a lever on a bearing. The lever is advantageously arranged and designed such that it can be actuated from outside the retaining device. By means of a corresponding actuation device for the lever on the automatic analysis apparatus, it is thus possible to precisely set the position of the needle in the axial direction. In particular, during the puncturing of the seal on a blood sampling tube, the lever is actuated in an automated manner and the needle is brought with its abutment to the maximum deflection position, such that it bears in the hollow space, does not perform any further movement in the puncturing procedure and is thereby stabilized.

Advantageously, an element of a position-measuring device is connected to the bolt. The element can vary depending on the nature of the position-measuring device, e.g. a microswitch can be provided, or a reflector element for a light barrier. In all cases, the movement of the bolt relative to the retaining device can be determined, such that the detection of a crash is permitted in a particularly simple way.

The first retaining element of a described retaining device is advantageously connected to a base plate of the automatic analysis apparatus, which base plate is movable in an automated manner.

Advantageously, the connection of the first retaining element to the base plate comprises a joint which, in a first position, prevents release of the first retaining element, by means of a form fit, and, in a second position, permits release of the first retaining element. A design of this kind combines, in a particularly simple way, the requirements of stable positioning and easy removability of the hollow needle. In the first position, release is ruled out by the form fit, such that stable positioning is ensured. When the joint is brought manually to the second position, the retaining device can easily be removed with the needle.

In another advantageous embodiment, the connection comprises a connection element, which connects the first retaining element to the base plate with a form fit and which, under the effect of a force, opens in a manner allowing it to reclose. The connection element thus serves to fix the connection of the first retaining element to the base plate in the first position of the joint. It is only by a corresponding force acting on the connection element that the joint can then be moved to the second position and the retaining device removed from the base plate. A new retaining device with a new hollow needle is fitted again, and the joint is turned to the first position. On account of the connection element being able to reclose, the retaining device is then fixed again in a simple way.

Various reclosable constructions are possible here as the connection element. A particularly stable hold with precise positioning is advantageously achieved if the connection element has rollers which are movable from a rest position in a self-restoring manner. These rollers should be arranged such that they are displaced under the effect of a force when the retaining device is pulled, and they thus permit a movement of the joint to the second position and the removal of the retaining device.

The present invention further relates to an automatic analysis apparatus with a pipetting device comprising a hollow needle, wherein the pipetting device comprises a described retaining device for the hollow needle.

The advantages achieved with the invention are in particular that, on account of the hollow needle being mounted releasably in a retaining device as described, on the one hand a stable hold and a high level of positioning precision are achieved, and, on the other hand, easy replacement of a worn hollow needle is permitted. The construction thus facilitates the automated removal of sample liquids from sealed sample containers in an automatic analysis apparatus.

Figure 2:
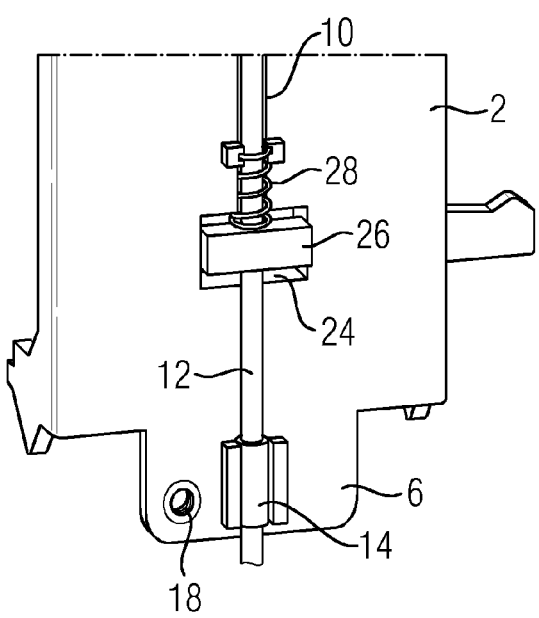
Figure 3:
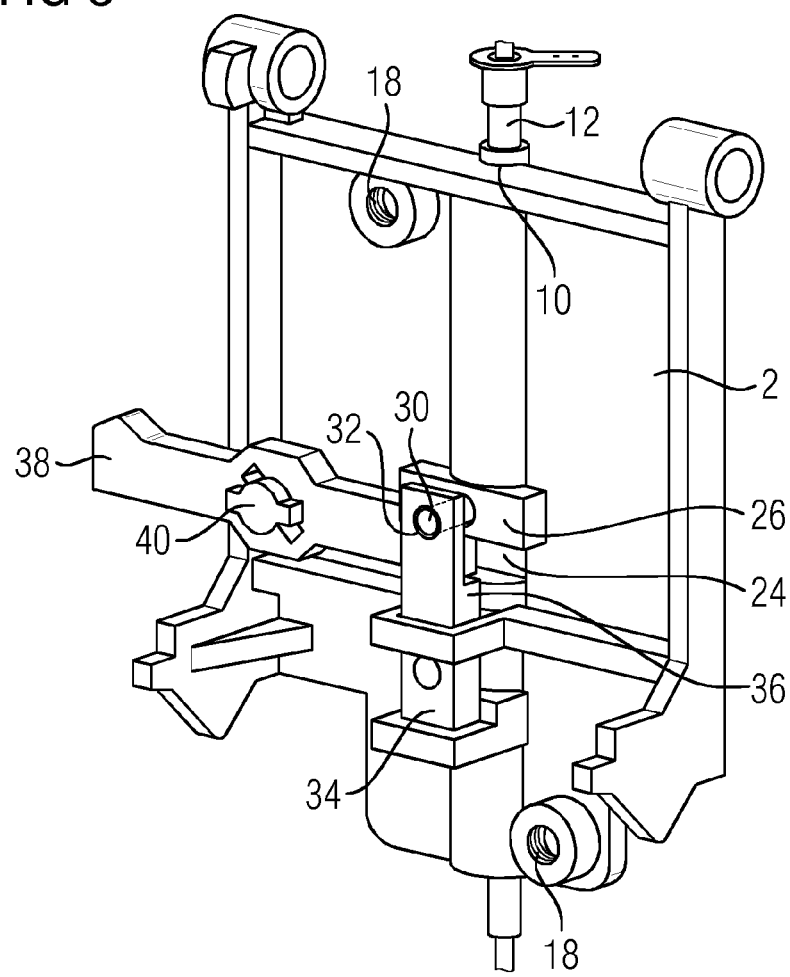
Figure 4:
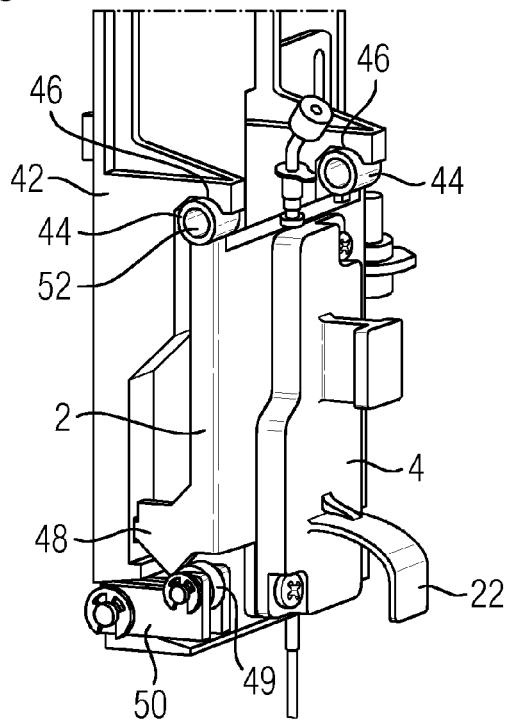
Figure 5:
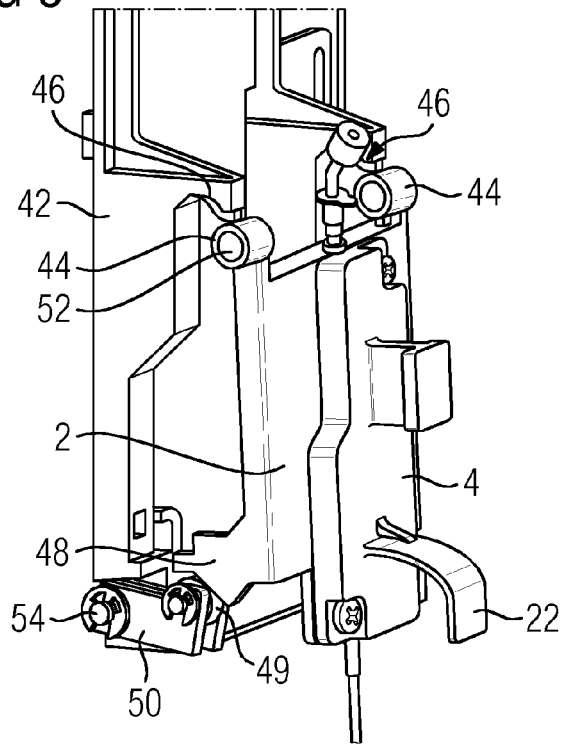

The invention is explained in more detail with reference to a drawing, in which:

FIG. 1 shows the first retaining element and second retaining element of a retaining device with an inserted hollow needle, in a position in which the elements are released from each other, FIG. 2 shows the first retaining element from the front, with a view of the hollow space, FIG. 3 shows the first retaining element from the rear, with the lever for actuating the position of the hollow needle, FIG. 4 shows the retaining device with base plate in the connected state, FIG. 5 shows the retaining device with the joint released, and FIG. 6 shows details of the connection element of the retaining device with the joint released.

Identical parts are provided with the same reference signs in all of the figures.

FIG. 1 shows the retaining device 1 with first retaining element 2 and second retaining element 4. The first retaining element 2 has a substantially rectangular and flat basic shape, with a projection 6 extending in the direction of a receiving position (not shown) for blood samping tubes. Extending centrally from the projection 6 as far as the edge 8 of the first retaining element 2 lying opposite the projection 6, there is a groove 10 in which a cylindrical hollow needle 12 is guided. The terms axial and radial, as used below, always relate to the cylinder shape of the hollow needle.

The hollow needle 12 is mounted in two bearing bushings 14, which are arranged in the area of the edge 8 and on the projection 6. The hollow needle 12 extends beyond the groove 10. On the side of the edge 8, it has an attachment 15 for a hose for subjecting the cavity of the hollow needle 12 to pressure or negative pressure. On the side of the projection 6, the hollow needle 12 extends as far as its tip (not shown) for puncturing the seal of a blood sampling tube.

The second retaining element 4 has bores into which screws 16 can be inserted. By means of corresponding threaded bores 18 in the first retaining element 2, the second retaining element 4 can be fixed on the first retaining element. The second retaining element 4 is designed such that it extends along the entire groove 10 of the first retaining element 2 and has a groove 20 that is congruent to the groove 10 on the first retaining element 2. In the connected state, the hollow needle 12 is thus fixed between the retaining elements 2, 4 in the bearing bushings 14 and is movable only in the axial direction.

The second retaining element has grips 22 for easy removal of the retaining device 1. The removal procedure is explained in FIGS. 4 to 6. The other features already shown in FIG. 1 are likewise explained in more detail below.

FIG. 2 shows the lower part of the first retaining element 2 in an enlarged view. The first retaining element 2 has a block-shaped hollow space 24, which interrupts the groove 10. A similarly block-shaped abutment 26 is arranged fixedly on the hollow needle 12 and completely fills the hollow space 24 in the radial plane, but has less height than the hollow space 24 in the axial direction. The axial movement of the hollow needle 12 in the groove 10 is thus limited to the difference in height between abutment 26 and hollow space 24.

A spring 28 connects the abutment 26 and the first retaining element 2, such that the position of the hollow needle is self-restoring in the axial direction. FIG. 1 shows the rest position, i.e. with no force applied, while FIG. 2 shows the position in a crash state, i.e. with force applied to the needle tip.

FIG. 3 shows, in contrast to FIG. 2, the rear face of the upper part of the first retaining element 2. A bolt 30 is secured to the rear face of the abutment 26 and is mounted in a bore 32 of a block 34 that is movable in the axial direction. The block 34 has a shoulder 36 directed toward the front face. Between the shoulder 36 and the bolt 30, a gap is provided in which an end of a lever 38 engages, which lever 38 is mounted on the first retaining element 2 via a shaft 40 and has its free end protruding beyond the edge of the first retaining element 2. At the free end of the lever 38, therefore, the axial position of the hollow needle 12 can be influenced from outside the retaining device 1. This takes place, for example, when puncturing a seal of a blood sampling tube. By means of a device (not shown in detail) of the automatic analysis apparatus, the lever 38 is actuated such that the hollow needle 12 is brought to the position shown in FIG. 2. In this way, the hollow needle 12 is stabilized during the puncturing.

An element (not described in detail) of a position-measuring device is arranged on the block 34. For example, this element can be a reflector for a light barrier, a microswitch or the like. In this way, the position of the hollow needle 12 relative to the retaining element 2 can be determined and a crash can be reliably detected.

FIG. 4 shows the retaining elements 2, 4 from FIG. 1 when connected by means of screws 16 and arranged as a retaining device 1 on a base plate 42. The base plate 42 is connected to an electric or hydraulic motor (not shown) and, during the analysis, can therefore be moved in an automated manner by the control unit of the automatic analysis apparatus.

The securing of the retaining device 1 to the base plate 42 by means of the first retaining element 2 is effected via hollow cylinders 44, which are fixedly arranged at both ends of the edge 8 of the first retaining element 2. They engage in bearings 46 that are cut out in a trapezoidal shape on the base plate 42 and that are adapted to the hollow cylinders 44. The trapezoidal shape of the bearings 46, in conjunction with the hollow cylinder shape, permits a bearing with particularly precise positioning. At its lower part, the first retaining element 2 has projections 48 which are directed toward the base plate 42 and which, together with movable and self-restoring rollers 49, form a connection element 50 which connects the first retaining element 2 to the base plate 42 with a form fit and, under the effect of a force, opens in a way allowing it to reclose. Here too, the round shape of the rollers 49, in conjunction with a wedge-shaped indent of the projection 48, ensures precise automatic adjustment. In the first position of the joint 52 composed of hollow cylinders 44 and bearings 46 shown in FIG. 4, the retaining element 2 is connected to the base plate 42 with a form fit.

The release of the retaining element 2 in order to replace the hollow needle 12 is shown in FIGS. 5 and 6. When the grip 22 is pulled by hand, this causes a movement of the rollers 49, which are mounted with a self-restoring function by way of a shaft 54. In this way, the retaining element 2 is released in the connection element 50 and swiveled out in the joint 52. With the loss of the form fit in the connection element 50, the hollow cylinders 44 can be released from the bearings 46. With a sufficient pull, the retaining device 1 can thus be removed (see FIG. 5).

FIG. 6 shows an enlarged view of a self-restoring roller 49 mounted in the shaft 54.

A replacement needle is supplied to the user directly in a new retaining device 1. Installation takes place in the reverse sequence. Thus, simple replacement of a worn hollow needle 12 is possible, and precise positioning remains ensured.

LIST OF REFERENCE SIGNS 1 retaining device
2 first retaining element
4 second retaining element
6 projection
8 edge
10 groove
12 hollow needle
14 bearing bushing
15 attachment
16 screw
18 threaded bore
20 groove
22 grip
24 hollow space
26 abutment
28 spring
30 bolt
32 bore
34 block
36 shoulder
38 lever
40 shaft
42 base plate
44 hollow cylinder
46 bearing
48 projection
49 rollers
50 connection element
52 joint
54 shaft

The invention claimed is:

1. A retaining device for a hollow needle for puncturing the lid of a blood sampling tube in an automatic analysis apparatus, comprising a base plate, a first retaining element, which can be secured releasably on the base plate forming a connection there between, wherein the base plate is movable in an automated manner, and a second retaining element, which is connected to the first retaining element, wherein at least one bearing bushing is provided, which is fixed between the first and second retaining elements and in which the hollow needle is mounted, and wherein the connection of the first retaining element to the base plate comprises a joint which, in a first position, prevents release of the first retaining element, by means of a form fit, and, in a second position, permits release of the first retaining element.

2. The retaining device as claimed in claim 1, in which the first retaining element comprises a hollow space in which an abutment, secured on the hollow needle, is enclosed in such a way that the movement of the hollow needle in the at least one bearing bushing is limited.

3. The retaining device as claimed in claim 2, in which a restoring element is assigned to the hollow needle.

4. The retaining device as claimed in claim 3, in which the restoring element is a spring secured between the abutment and the first retaining element.

5. The retaining device as claimed in claim 2, in which the abutment comprises a bolt, which is connected to a lever mounted in a bearing.

6. The retaining device as claimed in claim 5, in which an element of a position-measuring device is connected to the bolt.

7. The retaining device as claimed in claim 1, in which the first retaining element is connected releasably to a base plate of the automatic analysis apparatus, which base plate is movable in an automated manner.

8. The retaining device as claimed in claim 1, in which the connection comprises a connection element, which connects the first retaining element to the base plate with a form fit and which, under the effect of a force, opens in a manner allowing it to reclose.

9. The retaining device as claimed in claim 8, in which the connection element has rollers, which are movable from a rest position in a self-restoring manner.

10. An automated analysis apparatus with a pipetting device comprising a hollow needle, characterized in that the pipetting device comprises the retaining device for the hollow needle as claimed in claim 1.

* * * * *